US011208420B2

(12) United States Patent
Sadler et al.

(10) Patent No.: US 11,208,420 B2
(45) Date of Patent: Dec. 28, 2021

(54) PROCESS TO PRODUCE BLENDED (METH)ACRYLATE/VINYL ESTER RESIN CROSS-LINKERS

(71) Applicants: DREXEL UNIVERSITY, Philadelphia, PA (US); The Government of the United States of America as Represented by the Secretary of the Army, Adelphi, MD (US)

(72) Inventors: Joshua Matthew Sadler, Middle River, MD (US); John Joseph La Scala, Wilmington, DE (US); Giuseppe R. Palmese, Hainesport, NJ (US)

(73) Assignees: Drexel University, Philadelphia, PA (US); THE UNITED STATES OF AMERICA AS REPRESENTED BY THE SECRETARY OF THE ARMY, Washington, DC (US)

( * ) Notice: Subject to any disclaimer, the term of this patent is extended or adjusted under 35 U.S.C. 154(b) by 18 days.

(21) Appl. No.: 16/462,741

(22) PCT Filed: Nov. 16, 2017

(86) PCT No.: PCT/US2017/062038
§ 371 (c)(1),
(2) Date: May 21, 2019

(87) PCT Pub. No.: WO2018/098011
PCT Pub. Date: May 31, 2018

(65) Prior Publication Data
US 2019/0315763 A1    Oct. 17, 2019

Related U.S. Application Data

(60) Provisional application No. 62/425,220, filed on Nov. 22, 2016.

(51) Int. Cl.
*C07D 493/04* (2006.01)
*C08G 59/42* (2006.01)
(Continued)

(52) U.S. Cl.
CPC ....... *C07D 493/04* (2013.01); *C08G 59/1466* (2013.01); *C08G 59/42* (2013.01);
(Continued)

(58) Field of Classification Search
CPC ......... C08L 33/04–16; C08L 63/00–10; C08L 33/14; C08G 59/1455–1466; C09D 133/14; C09J 133/14; C08F 20/26
See application file for complete search history.

(56) References Cited

U.S. PATENT DOCUMENTS 2,143,924 A   1/1939   Rubenstein
3,041,300 A   6/1962   Morrison et al.
(Continued)

FOREIGN PATENT DOCUMENTS

EP   2808361 A   3/2014
GB    586141 A   3/1947
(Continued)

OTHER PUBLICATIONS

Dow Chemical Company, Dow Liquid Epoxy Resins (1999).*
(Continued)

*Primary Examiner* — Kregg T Brooks
(74) *Attorney, Agent, or Firm* — Mendelsohn Dunleavy, P.C.

(57) ABSTRACT

This invention outlines a method for synthesizing a blended resin system in a one pot reaction that may utilize, for example, bio-based anhydrosugars such as isosorbide as a principle component to produce isosorbide dimethacrylate and other monomeric materials for thermosetting applications. This invention establishes a one-pot procedure for
(Continued)

reacting a hydroxy group containing compound with methacrylic anhydride in the first step and using the by-product methacrylic acid to react with glycidyl ethers to form additional methacrylate compounds in the second step. This methodology can be formulated to produce a wide array of resin systems that have controlled ratios of hydroxy group containing compound/crosslinker/reactive diluent. Additionally, the novel resin systems may be partially to fully biobased, promoting global sustainability and reducing costs, and when free radically polymerized have properties that meet or exceed their petroleum derived counterparts.

27 Claims, 3 Drawing Sheets

(51) Int. Cl.
    *C08L 63/00*     (2006.01)
    *C08G 59/16*     (2006.01)
    *C08L 33/08*     (2006.01)
    *C08L 33/10*     (2006.01)
    *C08G 59/17*     (2006.01)

(52) U.S. Cl.
    CPC .......... *C08G 59/4238* (2013.01); *C08L 63/00* (2013.01); *C08L 33/08* (2013.01); *C08L 33/10* (2013.01); *C08L 2312/00* (2013.01)

(56) References Cited

U.S. PATENT DOCUMENTS

| | | | |
|---|---|---|---|
| 3,272,845 A | 9/1966 | Zech et al. | |
| 3,278,618 A * | 10/1966 | Amagasa | C07C 13/20 585/380 |
| 4,205,018 A * | 5/1980 | Nagasawa | C08F 290/06 427/507 |
| 4,246,161 A * | 1/1981 | Smith | C08G 59/68 310/43 |
| 4,284,747 A * | 8/1981 | Griffith | C08G 59/4207 525/530 |
| 4,495,341 A | 1/1985 | Stamberger | |
| 4,595,763 A | 6/1986 | Renga et al. | |
| 4,745,138 A * | 5/1988 | Thanawalla | C08F 8/14 522/120 |
| 5,096,938 A * | 3/1992 | Beck | C09D 167/07 522/100 |
| 5,516,860 A * | 5/1996 | Reich | C08G 59/1466 525/531 |
| 6,107,362 A * | 8/2000 | Koniger | C08F 299/026 522/103 |
| 6,121,398 A | 9/2000 | Wool et al. | |
| 6,825,242 B2 | 11/2004 | Sulzbach et al. | |
| 7,619,056 B2 | 11/2009 | East et al. | |
| 7,723,461 B1 | 5/2010 | Wagener et al. | |
| 2003/0139489 A1 | 7/2003 | Sulzbach et al. | |
| 2003/0181763 A1 | 9/2003 | Murata et al. | |
| 2009/0198040 A1* | 8/2009 | Kurata | H01B 3/20 528/365 |
| 2009/0275715 A1 | 11/2009 | Boyles et al. | |
| 2014/0200288 A1 | 7/2014 | Jin et al. | |
| 2014/0249285 A1 | 9/2014 | Palmese et al. | |
| 2016/0251371 A1 | 9/2016 | Misske et al. | |

FOREIGN PATENT DOCUMENTS

| | | |
|---|---|---|
| WO | WO2011048739 A1 | 4/2011 |
| WO | WO2013066461 A2 | 5/2013 |

OTHER PUBLICATIONS

Liu et al., "Biobased Thermosets Prepared from Rigid Isosorbide and Flexible Soybean Oil Derivatives," ACS Sustainable Chem. & Eng. (2017) 5, 774-783 (published Nov. 7, 2016).*
Stanzione III, Joseph F., et al. "Vanillin-based resin for use in composite applications." Green Chemistry 14.8 (2012): 2346-2352.
Sadler, Joshua M. et al., "Isosorbide-methacrylate as a bio-based low viscosity resin for high performance thermosetting applications." Journal of Materials Chemistry A 1.40 (2013): 12579-12586.
International Search Report for International Patent Application No. PCT/US2017/062038; dated Feb. 21, 2018.
ISA Written Opinion for International Patent Application No. PCT/US2017/062038; dated Feb. 21, 2018.
Cardinale, Daniela, et al. (editors), "Enzyme Nanocarriers." CRC Press, Florida, USA (2015): pp. 124.

* cited by examiner

PROCESS TO PRODUCE BLENDED (METH)ACRYLATE/VINYL ESTER RESIN CROSS-LINKERS

STATEMENT OF GOVERNMENT INTEREST

This invention was made with government support under ARL Cooperative Agreement W911NF-15-2-0017, direct from the U.S. Army Research Laboratory. The Government has certain rights in this invention.

BACKGROUND OF THE INVENTION

Field of the Invention

Processes for making curable and cured vinyl ester resin systems for high performance applications using bio-based (meth)acrylates derived from non-petroleum celluloses or carbohydrates with a core scaffold of isosorbide are disclosed. More specifically, a one pot, two-step synthesis method has been developed which makes the bio-based (meth)acrylate monomers and then cross-links vinyl ester resins with the monomers.

Description of the Related Technology

Vinyl ester resins are thermosetting polymers that are commonly used in variety of applications ranging from adhesives, coatings, composites and the resin matrices for fiber reinforced composites. There are many desirable properties of vinyl ester resins, such as strength, toughness, low cost, low weight, and their particular viscosities for processing prior to curing, which are the reasons that vinyl ester resins have such wide acceptance in military and commercial uses. Vinyl ester resins are used extensively in a number of commercial applications and are due to their ease of processing and enhanced performance provide a 13 billion/year industry. The vinyl ester resins used in these applications are usually blended from a number of different petroleum derived monomers to produce a resin system that meets the application criteria.

Viscosity is a key factor for determining the utility of vinyl ester resins because lower viscosity curable resins are easier to work with and may be prepared using a wider variety of methods. Petroleum-based vinyl ester resins are typically high molecular weight species that are often extremely viscous. Thus, they often require reactive diluents in order to reduce the viscosity of the curable resin so that the resins can be processed. Typical reactive diluents, such as styrene, are generally regarded as Hazardous Air Pollutants (HAPs) and/or Volatile Organic Compounds (VOCs) the use of which is controlled by the Environmental Protection Agency (EPA). Significant research efforts have been devoted to finding ways to eliminate or reduce the use of these potentially hazardous reactive diluents.

Another factor that hinders wider acceptance of vinyl ester resins is that they are typically derived from petroleum products. Petroleum is a commodity with well-known price volatility. Also, environmental costs of using petroleum are very high.

Vinyl ester resins derived from renewable sources can reduce dependency on petroleum and thus are important for ensuring the continued use and development of thermosetting polymers and composites. Bio-refining of material based on converting biomass into vinyl ester products has been successfully developed. For example, bio-refining of triglycerides and carbohydrates can be used to produce a wealth of new fine chemicals that are useful for the development of bio-based polymers. Fatty acids and triglycerides have also been successfully developed into materials ranging from toughening agents and plasticizers to reactive diluent replacements.

U.S. Pat. No. 6,121,398 (Wool et al.) discloses functionalized triglycerides derived from plant oil that are polymerizable, and their use to produce high modulus polymers. The functionalized triglycerides may be produced via several different chemical synthesis routes. For example, epoxidized triglycerides may be produced and converted to resilient rubbers by control of the molecular weight and cross-link density. The resultant rubbers can be used as rubber toughening agents in rigid composites. In the examples of this patent, acrylate-based resins are prepared by reacting the epoxidized triglycerides with acrylic materials such as acrylic acid. The thermosetting resins prepared by this method are said to have properties similar to commercially available bisphenol-A vinyl ester resins. Other functionalized triglycerides are described in U.S. Pat. No. 6,825,242 and U.S. patent application publication nos. US 2003/0139489 and US 2009/0275715.

Besides triglycerides, anhydrosugars derived from cellulose or carbohydrates, such as isosorbide, isomannide and isoidide, have also been explored for use as reactive monomers. These anhydrosugars are useful building blocks because they provide a rigid bicyclic core structure that can be developed into resins. For example, anhydrosugars such as bis-anhydrohexitols, have been fashioned into epoxy resins by forming the corresponding glycidyl ethers, as described in U.S. Pat. No. 3,041,300 (Zech, et al.) and U.S. Pat. No. 3,272,845 (Morrison, et al.).

U.S. Pat. No. 7,619,056 (Jaffe, et al.) describes a different synthesis process whereby the glycidyl ethers of the anhydrosugars can be obtained, and subsequently cured with polyamines to form thermosets. WO 2011/048739 A1 discloses (meth)acrylate monomers which have cyclic structures of the formula:

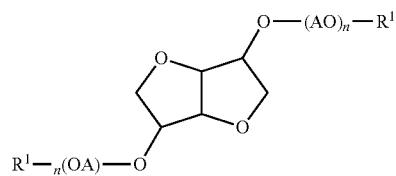

wherein each $R^1$ is a hydrogen atom or (meth)acryloyl, with at least one $R^1$ being (meth)acryloyl, A is a $C_{2-4}$ alkylene and n is a number from 0 to 30.

GB 586 141 A discloses a method wherein polyhydric alcohols or their anhydrides or hexose derivatives are treated in caustic soda solution with the acid chlorides of unsaturated acids or in pyridine solution with the anhydrides of unsaturated acids to provide esters. The esters are then polymerized by heating for a few minutes to the melting point or any other suitable temperature.

U.S. Pat. No. 7,723,461 B1 discloses polymers including components produced from renewable resources and methods for making them. The polymers are made by polymerizing reactive intermediates derived from lactide or sorbitol with each other or with other resins. The intermediates can be used to prepare vinyl ester-styrene resins and thermoset networks formed therefrom.

The article, "Vanillin-Based Resin for Use in Composite Applications," *Green Chemistry*, 2012, 14 (8), 2346-23522, by J. R. Stanzione et al. discloses a method to convert vanillin into reactive diluent methacrylate and utilize the excess methacrylic acid to react with glycidyl methacrylate to form a low performance cross linker, glycidyl dimethacrylate.

It is desirable to develop other methods for using anhydrosugars to produce low viscosity thermosetting vinyl ester resins. Reactive diluents such as styrene are still commonly used for reducing viscosity of these bio-based resins. Commercial practice involves reducing the styrene content in the resin to about 33 wt. % styrene, which makes the resin barely acceptable for composite manufacturing applications. In addition, reducing the styrene content significantly reduces the toughness of the resins.

There remains a need to provide bio-based vinyl ester resins with excellent processability and an acceptable toughness which can be produced using a cost effective method and with a reduced dependency on reactive diluents.

WO 2013/066461 A1 and the article "Isosorbide-Methacrylate as a Bio-Based Low Viscosity Resin for High performance Thermosetting Applications" *Journal of Materials Chemistry A*, 2013, 1(40), 12579-12586 describe methods to produce isosorbide methacrylate that require the removal of two equivalents of methacrylic acid by-product via standard separation methods.

SUMMARY OF THE INVENTION

In a first aspect, the disclosure relates to a method for producing a resin in a one-pot, two step reaction, the method includes:

i) reacting an organic compound having at least one hydroxy group with a (meth)acrylate to produce a reaction product containing a (meth)acrylic ester and (meth)acrylic acid;

ii) reacting said reaction product from step i) with at least one organic compound containing at least one epoxy group to form a reaction product; and iii) optionally blending the reaction product from step ii) with up to about 75 wt % of a reactive diluent, based on the total weight of the reaction product from step ii), to produce a curable resin.

In certain embodiments, the organic compound having at least one hydroxy group may be an alcohol, a sugar, a polyol including diols, and triols. Suitable sugars which may be used in the present invention include monosaccharides and disaccharides. Monosaccharides include galactose, glucose, lactose, gulose, fructose, galactose, idose, altrose, mannose, allose, ribose, xylose, lyxose, arabinose, talose, erythrose, threose, arabinoseerythrulose, ribulose, xylulose, psicose, sorbose, tagatose and glucoheptose. Disaccharides include sucrose, lactulose, lactose, maltose, trehalose, and cellobiose, kojibiose, nigerose, isornaltose, sophorose, laminaribiose, gentiobiose, turanose, maltulose, palatinose, gentiobiulose, mannobiose, melibiose, melibiulose, rutinose, rutinulose, and xylobiose. Preferred sugars include, for example, glucose, sucrose, fructose, lactose, mannose and galactose.

The alcohol may be, for example, methanol, ethanol, propanol, butanol, pentanol, hexanol, cyclohexanol, and octanol. Suitable polyols include ethylene glycol, propylene glycol, polyethylene glycol oligomers, polypropylene glycol oligomers, hexanediol, glycerol, and pentaerythritol.

In certain embodiments, the organic compound having at least one hydroxy group may be a dihydroxy anhydrosugar, ethylene glycol, a $C_1$-$C_{20}$ alcohol, and any combination thereof. The dihydroxy anhydrosugar may be selected from the group consisting of isosorbide, isomannide, and isoidide. In certain embodiments, the dihydroxy anhydrosugar is isosorbide.

In each of the foregoing embodiments, step i) may employ a molar ratio of the at least one hydroxy group of the organic compound to the (meth)acrylate of from about 0.75 to about 1.25. In certain embodiments, step i) employs a molar ratio of isosorbide to (meth)acrylate from about 1:1.5 to 1:2.5.

In each of the foregoing embodiments, the (meth)acrylate may be methacrylic anhydride In each the foregoing embodiments, the molar ratio of (meth)acrylic acid to the epoxy group of the at least one organic compound containing at least one epoxy group may be from about 0.1 to about 1.2, or from about 0.9 to about 1.1.

In each of the foregoing embodiments, the organic compound containing at least one epoxy group may be at least one glycidyl ether selected from mono- and polyglycidyl ethers. In each of the foregoing embodiments, the organic compound containing at least one epoxy group may be selected from epoxidized oils, such as soybean oil and linseed oil, epoxidized cardanol, and epoxidized ricinoleic acid compounds (e.g. castor oil), can also be used in addition to or in place of the glycidyl ethers.

In all the foregoing embodiments, step ii) may be carried out at a temperature of 25° C. to about 100° C.

In all the foregoing embodiments, the reactive diluent may be selected from the group consisting of: styrene, 2-hydroxymethacrylate, methyl methacrylate, methyl acrylate, furfuryl methacrylate, methacrylated lauric acid and methacrylated fatty acids.

In all the foregoing embodiments, the at least one glycidyl ether may be selected from the group consisting of diglycidyl ether of bisphenol A (DGEBA) and blends of DGEBA oligomers such as those under the tradename Epon™, including Epon™ 825, 828, 834, 836, 100F, 1002F, 1004F, 1007F, 1009F, diglycidyl ether of bisphenol F, diglycidyl ether of bisguiaicol F, glycidyl acrylate, glycidyl methacrylate, phenyl glycidyl ether, acrylated glycidyl ethers of bisphenol, and methacrylated glycidyl ethers of bisphenol. In certain embodiments, the glycidyl ether comprises diglycidyl ether of bisphenol A or oligomers of diglycidyl ether of bisphenol A. In some embodiments, the glycidyl ether comprises a mixture of diglycidyl ether of bisphenol A and phenyl glycidyl ether in a molar ratio of 0.1 to 99 and preferably 0.9 to 1.1.

In certain embodiments, the method for producing a resin further comprises a step of curing the resin, wherein the curing is carried out by free-radical curing.

In certain embodiments, the glycidyl ether comprises a monoglycidyl ether, and the curable resin has a viscosity of about 50 cP to about 5000 cP at 20° C.

In certain embodiments, the glycidyl ether comprises only polyglycidyl ethers and the resin contains no reactive diluent. In such embodiments, the curable resin may have a viscosity of about 100 cP to about 5000 cP.

In certain embodiments, the dihydroxy anhydrosugar is reacted with a methacrylate. In certain embodiments, the method further comprises the step of curing the curable resin by free radical curing to provide a cured resin.

In each of the foregoing embodiments, the glycidyl ether components may be comprised of at least one said monoglycidyl ether and at least one polyglycidyl ether. In such embodiments, the glycidyl ether may have a molar ratio of monoglycidyl ether to polyglycidyl ether of from about 0 to about 3. In each of these embodiments, the curable resin may have a glass transition temperature of from about 30° C. to about 250° C. In such embodiments, the curable resin may have a viscosity of about 100 cP to about 5000 cP. In such embodiments, the curable resin may have a Young's modulus of about 1 GPa to about 4 GPa.

Additional features and advantages of the disclosure may be set forth in part in the description which follows, and/or may be learned by practice of the disclosure. The features and advantages of the disclosure may be further realized and attained by means of the elements and combinations particularly pointed out in the appended claims.

It is to be understood that both the foregoing general description and the following detailed description are exemplary and explanatory only and are not restrictive of the disclosure, as claimed.

DETAILED DESCRIPTION OF THE PREFERRED EMBODIMENT(S)

Figure 1:
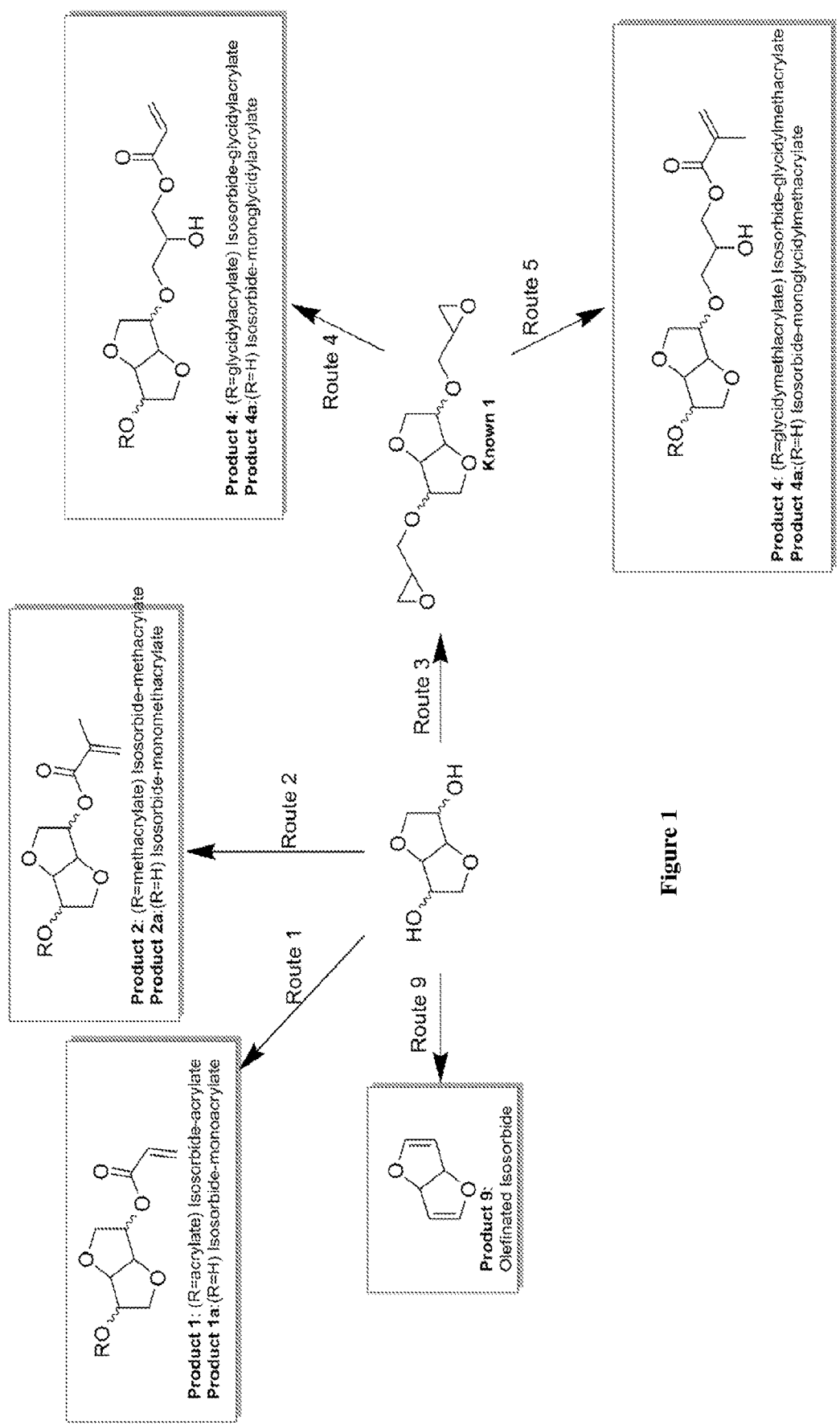
FIG. 1 is a schematic representation of various products that can be made from isosorbide.

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

Unless otherwise indicated, all numbers expressing quantities of ingredients, properties such as molecular weight, percent, ratio, reaction conditions, and so forth used in the specification and claims are to be understood as being modified in all instances by the term "about," whether or not the term "about" is present. Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

It is to be understood that each component, compound, substituent or parameter disclosed herein is to be interpreted as being disclosed for use alone or in combination with one or more of each and every other component, compound, substituent or parameter disclosed herein.

It is also to be understood that each amount/value or range of amounts/values for each component, compound, substituent or parameter disclosed herein is to be interpreted as also being disclosed in combination with each amount/value or range of amounts/values disclosed for any other component(s), compounds(s), substituent(s) or parameter(s) disclosed herein and that any combination of amounts/values or ranges of amounts/values for two or more component(s), compounds(s), substituent(s) or parameters disclosed herein are thus also disclosed in combination with each other for the purposes of this description.

It is further understood that each lower limit of each range disclosed herein is to be interpreted as disclosed in combination with each upper limit of each range disclosed herein for the same component, compounds, substituent or parameter. Thus, a disclosure of two ranges is to be interpreted as a disclosure of four ranges derived by combining each lower limit of each range with each upper limit of each range. A disclosure of three ranges is to be interpreted as a disclosure of nine ranges derived by combining each lower limit of each range with each upper limit of each range, etc. Furthermore, specific amounts/values of a component, compound, substituent or parameter disclosed in the description or an example is to be interpreted as a disclosure of either a lower or an upper limit of a range and thus can be combined with any other lower or upper limit of a range or specific amount/value for the same component, compound, substituent or parameter disclosed elsewhere in the application to form a range for that component, compound, substituent or parameter.

In one aspect, the present invention relates to a method of synthesizing vinyl ester resins in a one pot reaction, two step reaction, the method includes:

i) reacting a reacting an organic compound having at least one hydroxy group with a (meth)acrylate to produce a reaction product containing a (meth)acrylic ester and (meth)acrylic acid;

ii) reacting said reaction product from step i) with an organic compound containing at least one epoxy group; and iii) optionally blending the reaction product from step ii) with up to about 75 wt % of a reactive diluent, based on the total weight of the reaction product from step ii), to produce a curable resin.

In certain embodiments, the organic compound having at least one hydroxy group may be selected from an alcohol, a sugar such as a dihydroxy anhydrosugar, a polyol including diols, and triols. Suitable sugars include, for example, glucose, sucrose, fructose, lactose, mannose galactose, etc. The alcohol may be, for example, methanol, ethanol, propanol, butanol, pentanol, hexanol, cyclohexanol, furfuryl alcohol and octanol. Suitable polyols include ethylene glycol, propylene glycol, polyethylene glycol oligomers, polypropylene glycol oligomers, hexanediol, glycerol, and pentaerythritol. Other suitable compounds include 2-butyl-4-hydroxy-5-methyl-3(2H)-furanone and hydroxymethylfurfural.

In certain embodiments, the organic compound having at least one hydroxy group may be a dihydroxy anhydrosugar, ethylene glycol, a $C_1$-$C_{20}$ alcohol, and any combination thereof. The dihydroxy anhydrosugar may be selected from the group consisting of isosorbide, isomannide, and isoidide. In certain embodiments, the dihydroxy anhydrosugar is isosorbide.

Thus, in the first step i) of the reaction of the present invention, the organic compound having at least one hydroxy group is methacrylated with methacrylic anhydride to produce a methacrylated monomer and methacrylic acid. The number of methacrylate groups in the monomer can be controlled based on a combination of the number of hydroxy groups in the initial organic compound having at least one hydroxy group, as well as by selection of the molar ratio of the methacrylic anhydride to the number of hydroxy groups in the organic compound having at least one hydroxy group.

Step i) of the reaction may be carried out in the presence of a basic catalyst for nucleophic reactions. Suitable basic catalysts for nucleophilic reactions are triethylamine, tributylamine, alkali metal carbonates, acetates, ethoxides, quinolone, pyridine, N,N-dimethylaminopyridine, 4-(dimethylamino)pyridine, pyridine, and other pyridine derivatives. Exemplary catalysts can be found in U.S. Pat. No. 4,595,763.

In step i) a molar ratio of the at least one hydroxy group of the organic compound to the (meth)acrylate may be from about 0.75 to about 1.25.

In certain embodiments, the present invention utilizes bio-based anhydrosugars, such as isosorbide, isomannide, and isoidide as a principle component to produce the corresponding (meth)acrylates such as isosorbide (meth)acrylate and other monomeric materials for thermosetting applications. One important feature of these anhydrosugar-based monomers is their relatively low molecular weight due to their confined core structure resulting from the limited carbon chain length of these naturally occurring sugars. The low molecular weights of these anhydrosugar-based monomers can be used to reduce the overall viscosity of vinyl ester resins containing them, which, in turn, can reduce the dependency on reactive diluents. This has the advantage of reducing the need for reactive diluents, yet still producing vinyl ester resins with acceptable toughness and processability.

The schematic below describes an exemplary embodiment of step i) of the synthesis of the vinyl ester resin of the present invention. The reactants in step i) of this exemplary embodiment comprise the dihydroxy anhydrosugar isosorbide and methacrylic anhydride. The isosorbide and methacrylic anhydride are reacted to produce isosorbide dimethacrylate and methacrylic acid:

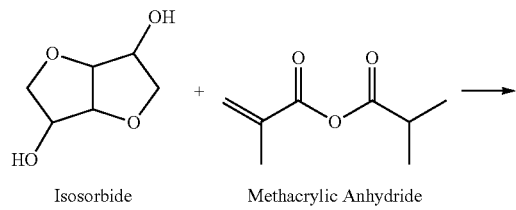

Isosorbide        Methacrylic Anhydride

-continued

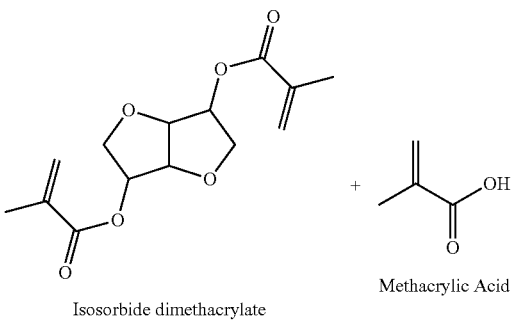

Isosorbide dimethacrylate        Methacrylic Acid

In this step i) of the exemplary embodiment, the isosorbide contains two hydroxy groups and sufficient methacrylic anhydride is employed to methacrylate the isosorbide to produce primarily dimethacrylated isosorbide monomer. The resultant isosorbide dimethacrylate is capable of free radical polymerization.

In certain embodiments, step i) employs a molar ratio of isosorbide to (meth)acrylate from about 1:1.5 to about 1:2.5. In certain embodiments, step i) employs a molar ratio of isosorbide to methacrylic anhydride of from about 1:1.5 to about 1:2.5. Step i) may preferably employ a basic catalyst for nucleophilic reactions known to those skilled in the art, such as 4-(dimethylamino)pyridine, pyridine, and other pyridine derivatives.

Following this step the isosorbide dimethacrylate and the by product, methacrylic acid, are further reacted in the presence of a catalyst and the organic compound containing at least one epoxy group to form isosorbide (meth)acrylate curable resins. In preferred embodiments, the reaction product of step i) may be reacted with mono- and/or polyglycidyl ether. A reactive diluent may be blended into the reaction mixture in an amount of 0 to about 75 wt. %, based on the total weight of the reaction mixture including the reaction product, the organic compound containing at least one epoxy group and the reactive diluent.

The glycidyl ether may be a mono- or polyglycidyl ether selected from the group consisting of diglycidyl ether of bisphenol A (DGEBA) and blends of DGEBA oligomers such as those sold under the tradename Epon™, including Epon™ 825, 828, 834, 836, 100F, 1002F, 1004F, 1007F, and 1009F, diglycidyl ether of bisphenol F, diglycidyl ether of bisguiaicol F, glycidyl acrylate, glycidyl methacrylate, phenyl glycidyl ether, acrylated glycidyl ethers of bisphenol, and methacrylated glycidyl ethers of bisphenol. In certain embodiments, the glycidyl ether comprises diglycidyl ether of bisphenol A or oligomers of diglycidyl ether of bisphenol A. In some embodiments, the glycidyl ether comprises a mixture of diglycidyl ether of bisphenol A and phenyl glycidyl ether in a molar ratio of 0.1 to 99. Hydrogenated versions of the glycidyl ethers and brominated versions of such glycidyl ethers can also be used.

Epoxidized oils, such as soybean oil and linseed oil, epoxidized cardanol, and epoxidized ricinoleic acid compounds (e.g. castor oil), can also be used as the organic compound containing at least one epoxy group in addition to, or in place of, the glycidyl ethers, despite the secondary nature of the oxirane rings. For the purposes of this invention, nearly any epoxidized organic species could be used.

This reaction is carried out at a temperature between 25° C. and 100° C. The schematic below depicts an embodiment of step ii):

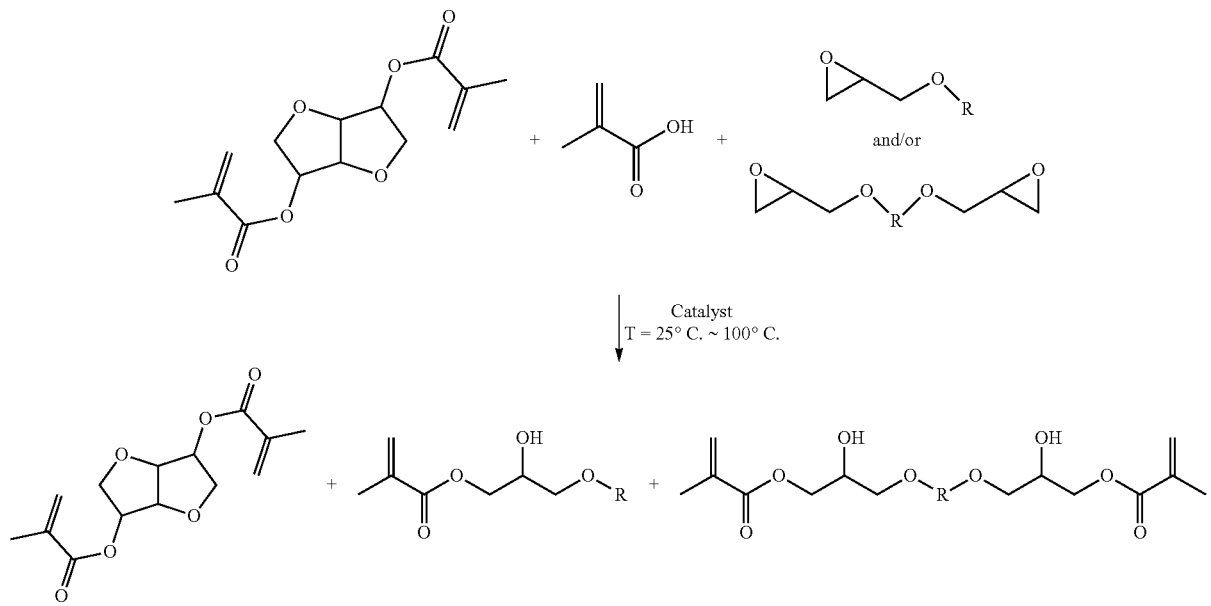

The reaction products of step i) include a (meth)acrylic ester and (meth)acrylic acid that can react with an epoxy functional molecule, resulting in the formation of methacrylated epoxy compounds. The epoxy compounds may include any of a number of different groups —R. Examples of such —R groups include acrylates, methacrylates, maleates, glycidyl ethers, or an alkyl, alkenyl or aryl substituent.

In some embodiments, it may be possible to carry out steps i) and ii) of the reaction essentially simultaneously in a single reactor rather than sequentially. In such embodiments, the organic compound with at least one hydroxy group, the methacrylic anhydride and the organic compound containing an epoxy group can be mixed together and reacted to form the desired product.

The catalyst for step ii) may be selected from trivalent chromium complexes, phthalate esters, hydroquinone, and other suitable catalysts known to a skilled person. A suitable catalyst may be the chromium based catalyst, AMC-2 ™ (Aerojet Chemicals, Rancho Cordova, Calif.). Alternatively, 0.1-3.0 wt. % of a 3:1 ratio of triphenyl antimony ($SbPh_3$) to triphenyl phosphine ($PPh_3$) may be used as a catalyst. Step ii) of the reaction may preferably be carried out under acidic conditions.

One advantage of the present invention is that the blended resin system may be produced on a bulk scale in a two-step, one-pot reaction. This obviates the need for separation, purification and blending steps that would otherwise be costly and would produce waste products requiring disposal. Instead of separating the (meth)acrylic acid by-product of the reaction step i), a glycidyl ether is used to react the by-product (meth)acrylic acid to produce a useful component of the reaction, thereby eliminating the need for separation of the (meth)acrylic acid from the isosorbide (meth) acrylate.

The dihydroxy anhydrosugars of the present invention may be selected from the group consisting of isosorbide, isomannide, isoidide and hydroxy-substituted species of these compounds. In certain embodiments of the present invention, the dihydroxy anhydrosugar is isosorbide or a hydroxy-substituted species thereof. In certain embodiments, the molar ratio of isosorbide to (meth)acrylate employed in reaction step i) is from about 0.5 to about 2.

In yet another aspect of the present invention, the anhydrosugar-based monomers may be used to adjust the glass transition temperature (Tg) of the vinyl ester resin to the desired level while also decreasing the viscosity. Because many bio-based reactive diluents have poor Tgs (homopolymers typically have Tgs below 0° C.), as compared to styrene, the anhydrosugar-based monomers of the present invention may be used to raise the Tg of the resin system using bio-based reactive diluents without increasing the overall viscosity. Specifically, the Tg of vinyl ester resins increases as the anhydrosugar-based monomer concentration increases. Thus, the anhydrosugar-based monomers may be used as Tg enhancers for vinyl ester resin systems. The Tg of the vinyl ester resins can be varied over a wide range of, for example, 25-250° C., depending primarily on the intended end use. The amount of anhydrosugar-based monomer in a particular vinyl ester resin system may be varied in order to achieve the desired Tg for the vinyl ester resin.

In another aspect of the present invention, the reaction may further comprise a step of curing the resin produced in step ii) or step iii) by free-radical curing. The methacrylate products may be treated with a free-radical initiator, with or without a promoter, in order to induce curing to form polymers. These polymers have properties comparable to petroleum-based vinyl ester derived polymers and exhibit highly advantageous stiffness and toughness and can have Tgs ranging from 0-250° C.

Exemplary reactive diluents suitable for use in the present invention are petroleum-based and bio-based compounds with a single polymerizable site. Suitable petroleum-based reactive diluents include, but are not limited to, styrene, 2-hydroxymethacrylate, methyl methacrylate, methyl acrylate, aryl-methacrylates, aryl-acylates, aliphatic methacrylates, aliphatic acrylates. Suitable bio-based reactive diluents include, but are not limited to, furfuryl methacrylate, tetrahydrofurfuryl methacrylate, furfuryl acrylate, tetrahydrofurfuryl acrylate, furioc acid glycidyl methacrylate (FA-GM), furioc acid glycidyl acrylate and methacrylated lauric acid, methacrylated octanoic acid, methacrylated fatty acids, and acrylated fatty acids.

In certain embodiments the glycidyl ether is present in an amount such that the molar ratio of (meth)acrylic acid to glycidyl ether reactive groups is from about 0.1 to about 1.2, or from about 0.4 to about 1.1, or from about 0.8 to about 1.1. In certain embodiments, a molar ratio of at least 1.2, of glycidyl ether to (meth)acrylic acid is preferred. An excess of glycidyl ether is preferred in certain embodiments as it promotes further functionalization of the resin by making available excess epoxy groups and it enables preparation of an epoxy-vinyl ester interpenetrating polymer network, if desired. Polymerization of the epoxy-functionalized materials can be achieved by cationic polymerization or addition of amines, such as diethylenetriamine, PACM, Epikure™ W, or anhydride epoxy curatives. In all the foregoing embodiments, the glycidyl ether may be selected from the group consisting of glycidyl acrylate, glycidyl methacrylate phenyl glycidyl ether, and acrylated glycidyl ethers of bisphenol. In certain embodiments, a slight excess of methacrylic acid to glycidyl ether is preferred to ensure complete conversion of the epoxy to methacrylate in order to maximize the performance of the methacrylate polymer resin.

In another embodiment of the present invention, the method comprises the step of curing the curable resin by free radical curing to provide a cured resin. In certain embodiments, the glycidyl ether comprises only a monoglycidyl ether, and the uncured resin has a viscosity of about 50 cP to about 500 cP. In the foregoing embodiment, the cured resin has a glass transition temperature from about 80'C to about 250° C. In the foregoing embodiment, the cured resin has a Young's modulus of from about 2 GPa to about 4 GPa.

In certain embodiments, the glycidyl ether comprises only a diglycidyl ether, and the uncured resin has a viscosity of about 250 cP to about 5000 cP. In the foregoing embodiment, the cured resin has a glass transition temperature from about 100° C. to about 250° C. In the foregoing embodiment, the cured resin has a Young's modulus of from about 2.5 GPa to about 4 GPa.

In some embodiments, the glycidyl ether comprises at least one of a monoglycidyl ether and at least one of a polyglycidyl ether. In this embodiment, the molar ratio of monoglycidyl ether to polyglycidyl ether is from about 0.5 to about 3, or from about 1 to about 2. In this embodiment, the method may further comprise the step of curing the curable resin by free-radical curing to provide a cured resin. The uncured resin has a viscosity of about 100 cP to about 5000 cP. The cured resin produced in this embodiment has a glass transition temperature from about 90'C to about 250'C and a Young's modulus of from about 1 GPa to about 4 GPa or from about 2 GPa to about 4 GPa.

In certain embodiments, in step i) the dihydroxy anhydrosugar is reacted with a methacrylate. The at least one glycidyl ether used to react with the reaction products of step i) in step ii) may comprise at least one monoglycidyl ether and at least one polyglycidyl ether. This method may further comprise the step of curing the curable resin by free radical curing to provide a cured resin.

A ternary resin system may also be formed by blending one or more anhydrosugar-based monomers with vinyl ester resins and reactive diluents. Ternary compositions will typically include up to 50%, more preferably, 5-15% by weight of reactive diluent(s) and 50-99%, more preferably, 85-95% by weight of vinyl ester cross-linker monomers, with the all weights being based on the total weight of the ternary mixture, wherein the composition of the cross-linker monomers is 25-55 molar % anhydrosugar-based monomers and 75-45 molar % of vinyl ester resin and/or unsaturated polyester monomer, more preferably, 48-52 molar % anhydrosugar-based monomers and 52-48 molar % of vinyl ester resin and/or unsaturated polyester monomer. The unsaturated polyester monomer may be made from one or more of the following components: phthalic acid, terephthalic acid, m-phthalic acid, suberic acid, adipic acid, succinic acid, maleic acid, fumaric acid, butylene glycol, propylene glycol, and ethylene glycol, but is not limited to unsaturated polyesters made therefrom.

Other exemplary compositions comprise 5-59% by weight by weight of anhydrosugar-based monomers, 5-95% by weight of methacrylate glycidyl ether (vinyl ester resin monomer), 0-75% by weight of an unsaturated polyester monomer and 0-75% by weight of at least one reactive diluent, or 15-50% by weight of anhydrosugar-based monomers, 15-50% by weight of methacrylate glycidyl ether, 0-50 wt % unsaturated polyester monomer and 0-50% by weight of at least one reactive diluent. The vinyl ester resin is preferably a petroleum-based vinyl ester.

The vinyl ester monomers may include, but are not limited to, commercial vinyl esters, which are vinyl esters that are commercially available, and which may be derived from any source. A broad range of commercial vinyl esters are suitable for use in the ternary resin systems of the present invention. Some examples of suitable vinyl esters are methacrylated/acrylated glycidyl ethers of bisphenols and novolac vinyl esters. Suitable bisphenols include bisphenol A, hexafluorobisphenol A, bisphenol E, bisphenol F, tetramethyl bisphenol E, tetramethyl bisphenol F, bisphenol M, bisphenol C, bisphenol P and bisphenol Z and bisphenol alternatives, such as bisguaiacol F and derivatives of such where the aromatic hydrogens are brominated or the aromatic units are hydrogenated. Methacrylates and acrylates of ethoxylated bisphenols may also be employed, as well as methacrylates and acrylates of epoxy products.

Vinyl esters with vinyl functionality greater than two may also be employed. Examples include acrylic and alkyl-acrylic vinyl esters of epoxy novolacs, and acrylates of tris-hydroxyphenylmethane glycidyl ether (THPM-GE), ethoxy phenol novolacs, and ethoxylated tris-hydroxyphenylmethane. In addition, derivatives of the above where the aromatic hydrogens are brominated or the aromatic units are hydrogenated, such as brominated bisphenol A based vinyl esters, may be employed. The preferred vinyl esters for use in the ternary systems of the present invention are the bisphenol vinyl esters due to the desirability of making structural composites from the resultant polymers.

In a ternary resin system, the anhydrosugar-based monomers of the present invention can be added to enhance the Tg of certain resins and/or to adjust the resin viscosity to improve the flow characteristics. The addition of the anhydrosugar-based monomers also increases the sustainability of the resins, and reduces or eliminates the reliance on reactive diluents, such as styrene, while maintaining or improving on the properties of petroleum-based resins. Use of the anhydrosugar-based monomers in varying concentrations in relation to the petroleum-based vinyl ester and reactive diluents components can allow for the tailoring of the resin properties for specific applications and the tailoring of the properties of polymeric materials that result from these resins.

The resins containing the anhydrosugar-based monomers can be cured using any method that makes use of free-radically initiated reactive curing systems, including, but not limited to thermal cure, room temperature cure, electron beam cure, and ultraviolet cure.

The anhydrosugar-based monomers can be polymerized to form linear, branched, hyperbranched, and cross-linked polymers for a wide array of applications, including biosensors, rheology modifiers, biomaterials, and polymerizable surfactants for media encapsulation. The anhydrosugar-based monomers can also be used for the production of polymer matrix composites, which are used in military, automotive, recreational, and marine applications. More specifically, the polymers can be used in automotive products, aircraft (e.g., skins for airframe structure), composite armor, marine vessels/equipment, sporting goods (skis, helmets, etc.). Adhesives based on such compounds are used various industrial environments including masonry, infrastructure (bridges, tunnels, wind turbines), armor, automotive, military adhesives for air, marine, and ground platforms, and electronics encapsulation. Exemplary products that may be made from these polymer matrix composites include body panels and armor for vehicles, composite hoods, and boat hull structures. In addition, these polymer matrix composites can be used with traditional thermosetting vinyl and polyester resins as a gel coating material to provide a protective coating for composites and other surfaces.

The use of anhydrosugar-based monomers as vinyl ester cross-linkers, Tg enhancers and viscosity modulators has been tested experimentally and found to be successful. Thermosetting liquid molding resins using anhydrosugar-based monomers to replace some or all of the petroleum based vinyl ester, or unsaturated polyester resin cross-linkers, blended with common reactive diluents, have also been found to have acceptable resin viscosities and polymer mechanical properties similar to those of commercially available petroleum-based vinyl ester/styrene polymers.

In another embodiment of the present invention, the method comprises the step of curing the curable resin that contains methacrylate and epoxy functionalities. In one embodiment, the curable resin can be cured by polymerization of the epoxy functionality followed by free radical polymerization of the methacrylate functionality to form a sequential interpenetrating polymer network. Alternatively, the curable resin can be cured by free radical polymerization of the methacrylate functionality followed by polymerization of the epoxy functionality to form a sequential interpenetrating polymer network.

The epoxy functionality can be polymerized by, for example, epoxy homopolymerization, an epoxy-amine polymerization reaction of the epoxy groups with an amine or an epoxy-anhydride polymerization reaction of the epoxy groups with an anhydride.

EXAMPLES

The following examples are shown using isosorbide as the starting point of the synthesis of the anhydrosugar-based monomers. The isosorbide may be substituted with either isomannide or isoidide to provide a similar outcome of the reaction, yielding similar resin systems that result in comparable polymer systems.

Example 1

Isosorbide (25.01 g, 171.13 mmol) and methacrylic anhydride (55.862 g, 347.57 mmol) were melted together at 55° C. before adding 4-dimethylamino pyridine (4-DMAP, 0.983 g, 8.046 mmol) and allowed to react until completion. When the methacrylic anhydride had been consumed, the reaction mixture was blended with Epon™ 828 (63.9 g) added and homogenized at 55° C. before adding an Aerojet AMC-2™ chromium catalyst (392.4 mg) and reacting until all epoxy functionalities had been consumed, as determined by NMR. The product appeared as a pale green gel.

The viscosity of the produced resin was relatively high like that of honey. The resin was cured using 1.5 wt % Trigonox™ and 0.375 wt % CoNap™ at room temperature and post-cured at 150° C. to provide a rigid and hard solid with a Tg in excess of 170° C. and a room temperature modulus of over 2 GPa.

Example 2

Isosorbide (170 mmol) and methacrylic anhydride (345 mmol) were melted together at 55° C. before adding 4-dimethylamino pyridine (4-DMAP, 0.983 g, 8.046 mmol) and allowed to react until completion. When the methacrylic anhydride had been consumed, the reaction mixture was blended with phenyl glycidyl ether (330 mmol) added and homogenized at 55° C. before adding an Aerojet AMC-2™ chromium catalyst (392.4 mg) and reacting until all epoxy functionalities had been consumed, as determined by NMR. The product appeared as a pale green gel.

The viscosity of the produced resin was fairly low like that of corn oil. The resin was cured using 1.5 wt % Trigonox™ and 0.375 wt % CoNap™ at room temperature and post-cured at 150° C. to provide a rigid and hard solid with a Tg in excess of 170° C. and a room temperature modulus of over 2 GPa.

Example 3

Sucrose (~100 mmol) and methacrylic anhydride (~620 mmol) are melted together at 55° C. before adding 4-dimethylamino pyridine (4-DMAP, 0.983 g, 8.046 mmol) and being allowed to react until completion. When the methacrylic anhydride is consumed, the reaction mixture is blended with Epon™ 828 (300 mmol) added and homogenized at 55° C. before adding an Aerojet AMC-2™ chromium catalyst (392.4 mg) and reacting until all epoxy functionalities are consumed. The resulting product is expected to be a high viscosity liquid.

Example 4

Ethylene glycol (~170 mmol) and methacrylic anhydride (~345 mmol) are mixed together at 55° C. before adding 4-dimethylamino pyridine (4-DMAP, 0.983 g, 8.046 mmol) and being allowed to react until completion. When the methacrylic anhydride is consumed, the reaction mixture is blended with Epon™ 828 (165 mmol) added and homogenized at 55° C. before adding an Aerojet AMC-2™ chromium catalyst (392.4 mg) and reacting until all epoxy functionalities are consumed. The resulting product is expected to be a medium viscosity liquid.

Example 5

Propanol (~170 mmol) and methacrylic anhydride (~175 mmol) are mixed together at 55° C. before adding 4-dimethylamino pyridine (4-DMAP, 0.983 g, 8.046 mmol) and being allowed to react until completion. When the methacrylic anhydride is consumed, the reaction mixture is blended with Epon™ 828 (85 mmol) added and homogenized at 55° C. before adding an Aerojet AMC-2™ chromium catalyst (392.4 mg) and reacting until all epoxy functionalities are consumed. The resulting product is expected to be a medium viscosity liquid.

Example 6

2-butyl-4-hydroxy-5-methyl-3(2H)-furanone (~170 mmol) and methacrylic anhydride (~345 mmol) are mixed together at 55° C. before adding 4-dimethylamino pyridine (4-DMAP, 0.983 g, 8.046 mmol) and being allowed to react until completion. When the methacrylic anhydride is consumed, the reaction mixture is blended with Epon™ 828 (165 mmol) added and homogenized at 55° C. before adding an Aerojet AMC-2™ chromium catalyst (392.4 mg) and reacting until all epoxy functionalities are consumed. The resulting product is expected to be a medium viscosity liquid.

Example 7

Hydroxymethylfurfural (~170 mmol) and methacrylic anhydride (~175 mmol) are mixed together at 55° C. before adding 4-dimethylamino pyridine (4-DMAP, 0.983 g, 8.046 mmol) and being allowed to react until completion. When the methacrylic anhydride is consumed, the reaction mixture is blended with Epon 828 (85 mmol) added and homogenized at 55° C. before adding an Aerojet AMC-2™ chromium catalyst (392.4 mg) and reacting until all epoxy functionalities are consumed. The resulting product is expected to be a low viscosity liquid.

Example 8

Isosorbide (~170 mmol) and methacrylic anhydride (~345 mmol) are melted together at 55° C. before adding 4-dimethylamino pyridine (4-DMAP, 0.983 g, 8.046 mmol) and being allowed to react until completion. When the methacrylic anhydride is consumed, the reaction mixture is blended with phenyl glycidyl ether (330 mmol) and homogenized at 55° C. before adding an Aerojet AMC-2™ chromium catalyst (392.4 mg) and reacting until all epoxy functionalities are consumed. The resulting product is expected to be a low viscosity liquid.

Example 9

Isosorbide (~170 mmol) and methacrylic anhydride (~345 mmol) are melted together at 55° C. before adding 4-dimethylamino pyridine (4-DMAP, 0.983 g, 8.046 mmol) and being allowed to react until completion. When the methacrylic anhydride is consumed, the reaction mixture is blended with Epon™ 828 (110 mmol) and phenyl glycidyl ether (110 mmol) and homogenized at 55° C. before adding an Aerojet AMC-2™ chromium catalyst (392.4 mg) and reacting until all epoxy functionalities are consumed. The resulting product is expected to be a medium viscosity liquid.

Example 10

Isosorbide (~170 mmol) and methacrylic anhydride (~345 mmol) are melted together at 55° C. before adding 4-dimethylamino pyridine (4-DMAP, 0.983 g, 8.046 mmol) and being allowed to react until completion. When the methacrylic anhydride is consumed, the reaction mixture is blended with epoxidized soybean oil (75 mmol) and homogenized at 55° C. before adding an Aerojet AMC-2™ chromium catalyst (392.4 mg) and reacting until all epoxy functionalities are consumed. The resulting product is expected to be a medium viscosity liquid.

Example 11

Isosorbide (~170 mmol) and methacrylic anhydride (~345 mmol) are melted together at 55° C. before adding 4-dimethylamino pyridine (4-DMAP, 0.983 g, 8.046 mmol) and being allowed to react until completion. When the methacrylic anhydride is consumed, the reaction mixture is blended with epoxidized soybean oil that is previously reacted with 2 equivalents of octanoic acid (150 mmol) and homogenized at 55° C. before adding an Aerojet AMC-2™ chromium catalyst (392.4 mg) and reacting until all epoxy functionalities are consumed. The resulting product is expected to be a medium viscosity liquid. The resulting solution is a bio-rubber vinyl functional toughened isosorbide-VE resin system.

Example 12

Isosorbide methacrylate and methacrylated Epon™ 828 are blended with 50 wt % styrene to produce a low viscosity liquid.

Example 13

Isosorbide methacrylate and methacrylated Epon™ 828 are blended with 50 wt % methacrylated lauric acid to produce a low viscosity liquid.

The liquids of Examples 12-13 can be cured using 1.5 wt % Trigonox™ and 0.375 wt % CoNap™ at room temperature and post-cured at 150° C. to provide a rigid and hard solid.

Example 14

Use of Methacrylic Acid in Less than a Stoichiometric Amount with Epon™ 828 to Produce an Interpenetrating Polymer Network (IPN)

Isosorbide (~170 mmol) and methacrylic anhydride (~345 mmol) are melted together at 55° C. before adding 4-dimethylamino pyridine (4-DMAP, 0.983 g, 8.046 mmol) and being allowed to react until completion. When the methacrylic anhydride is consumed, the reaction mixture is blended with Epon 828™ (200 mmol) added and homogenized at 55° C. before adding an Aerojet AMC-2™ chromium catalyst (392.4 mg) and reacting until all epoxy functionalities are consumed. The resulting resin is expected to be a medium viscosity liquid.

Example 15

Use of Less than a Stoichiometric Amount of Methacrylic Acid with Epoxidized Soybean Oil (ESO) or ESO/Furfuryl Alcohol (FA) (Bio-Rubber) to Produce an Interpenetrating Polymer Network (IPN)

Isosorbide (~170 mmol) and methacrylic anhydride (~345 mmol) are melted together at 55° C. before adding 4-dimethylamino pyridine (4-DMAP, 0.983 g, 8.046 mmol) and being allowed to react until completion. When the methacrylic anhydride is consumed, the reaction mixture was blended with epoxidized soybean oil (100 mmol) and homogenized at 55° C. before adding an Aerojet AMC-2™ chromium catalyst (392.4 mg) and reacting until all epoxy functionalities are consumed. The resulting product is expected to be a medium viscosity liquid.

Example 16

Comparison of Results Using the Method Described Herein with Baseline Results

Three different mixtures of isosorbide methacrylate and epoxy methacrylates were made using the method described herein. Four comparative examples were also run.

Experimental 1: Isosorbide and methacrylic anhydride were melted together before adding 4-dimethylamino pyridine (4-DMAP). The three component mixtures was allowed to react until completion. When the methacrylic anhydride had been consumed, the reaction mixture was blended with phenyl glycidyl ether and homogenized before adding an Aerojet AMC-2™ chromium or imidazole catalyst at 70-95° C. and reacting until all epoxy functionalities had been consumed, yielding a mixture of isosorbide methacrylate and a vinyl ester of polyglycidyl ether.

Experimental 2: Isosorbide and methacrylic anhydride were melted together before adding 4-dimethylamino pyridine (4-DMAP). The three component mixture was allowed to react until completion. When the methacrylic anhydride had been consumed, the reaction mixture was blended with DGEBA and homogenized before adding an Aerojet AMC-2™ chromium or imidazole catalyst at 70-95° C. and reacting until all epoxy functionalities had been consumed, yielding a mixture of isosorbide methacrylate and a vinyl ester of DGEBA.

Experimental 3: Isosorbide and methacrylic anhydride were melted together before adding 4-dimethylamino pyridine (4-DMAP). The three component mixture was allowed to react until completion. When the methacrylic anhydride had been consumed, the reaction mixture was blended with phenyl glycidyl ether and Bisphenol DGEBA and homogenized before adding an Aerojet AMC-2™ chromium or imidazole catalyst at 70-95° C. and reacting until all epoxy functionalities had been consumed, yielding a mixture of isosorbide methacrylate, a vinyl ester of polyglycidyl ether, and a vinyl ester of DGEBA.

Comparative Example 1

Vinyl ester of Bisphenol A diglycidyl ether (VE).

Comparative Example 2

A combination of a vinyl ester of Bisphenol A diglycidyl ether (VE) with styrene.

Comparative Examples 1 and 2 represent the baseline for the vinyl ester of Bisphenol A diglycidyl ether (VE).

Comparative Example 3

Isosorbide methacrylate.

Comparative Example 4

A combination of isosorbide methacrylate with styrene.

Comparative Examples 3 and 4 represent the baseline for isosorbide methacrylate.

Figure 2:
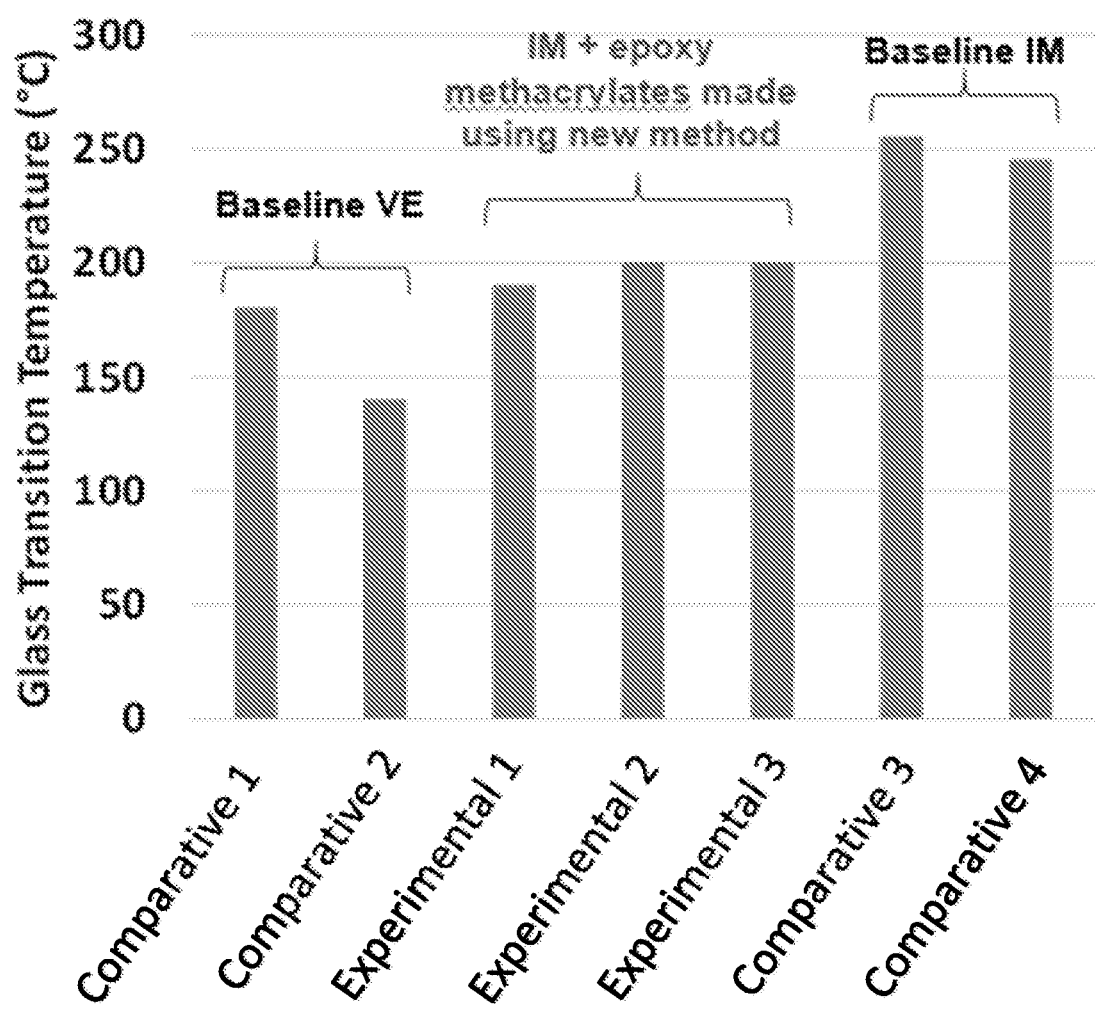
FIG. 2 is a graph showing the glass transition temperature results obtained in Example 16.
Figure 3:
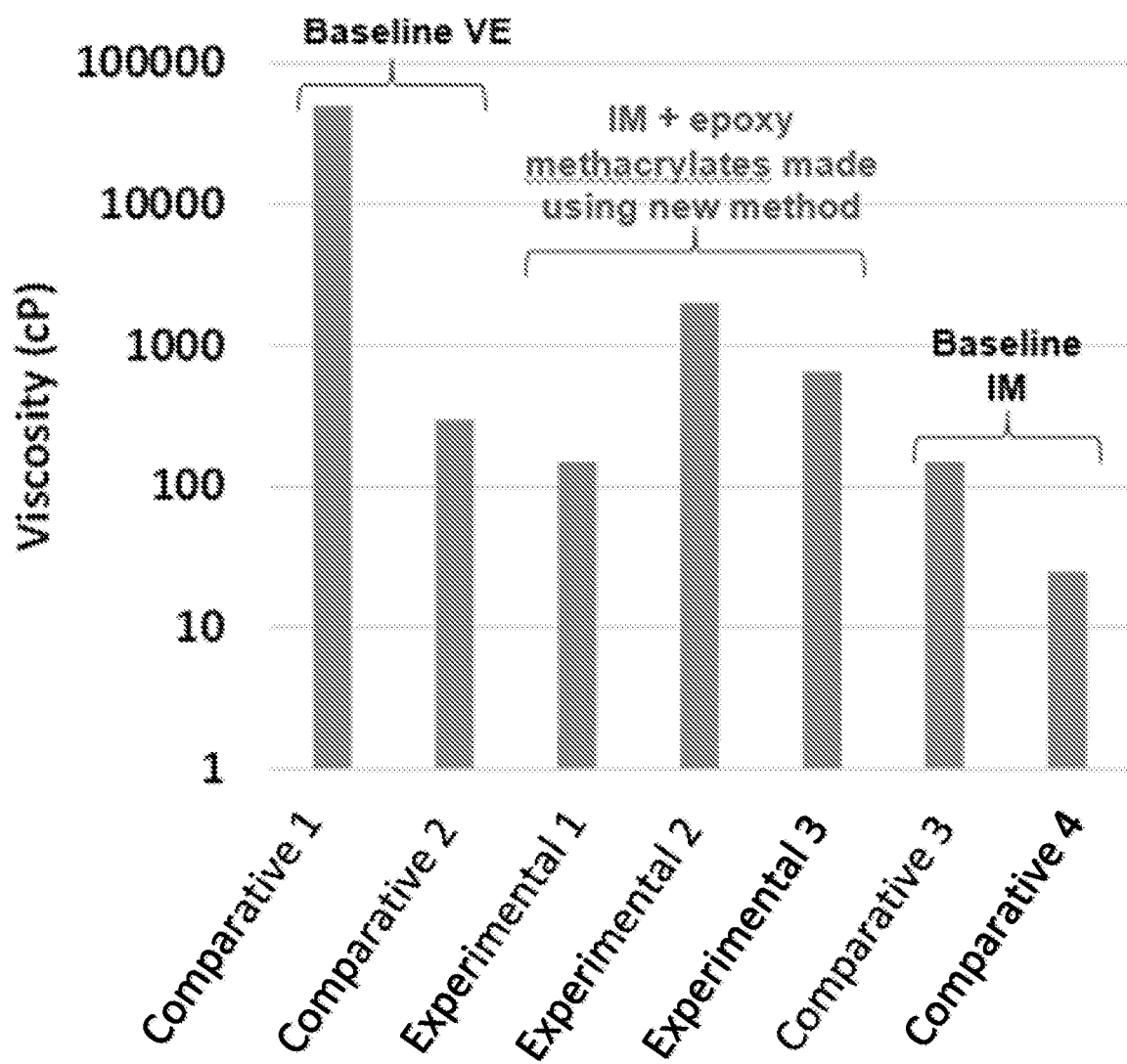
FIG. 3 is a graph showing the viscosity results obtained in Example 16.

The glass transition temperature (° C.) was determined for each of the examples using Dynamic Mechanical Analysis (DMA) methodology according to IOP L1047-033 as described in Joshua Sadler, Ian M McAninch, Faye R Toulan, Felicia Levine, and John J La Scala, Resin Characterization, ARL-SR0323, June 2015. The viscosity (cP) of these of the examples was measured using AR2000 Rheometer according to IOP L1047-020 as described in Joshua Sadler, Ian M McAninch, Faye R Toulan, Felicia Levine, and John J La Scala, Resin Characterization, ARL-SR0323, June 2015. The results for these tests are shown in FIGS. 2 and 3. The results show that the method described herein results in polymers where high Tg is achievable, and the Tg is tunable depending on the alcohols and epoxies used. The use of isosorbide methacrylate with the described methods increases Tg while reducing viscosity.

The foregoing embodiments are susceptible to considerable variation in practice. Accordingly, the embodiments are not intended to be limited to the specific exemplifications set forth herein. Rather, the foregoing embodiments are within the spirit and scope of the appended claims, including the equivalents thereof available as a matter of law.

All documents mentioned herein are hereby incorporated by reference in their entirety or alternatively to provide the disclosure for which they were specifically relied upon.

The applicant(s) do not intend to dedicate any disclosed embodiments to the public, and to the extent any disclosed modifications or alterations may not literally fall within the scope of the claims, they are considered to be part hereof under the doctrine of equivalents.

What is claimed is:

1. A method for producing a curable resin in a one-pot, two step reaction, said method comprising:
   i) reacting isosorbide with a (meth)acrylic anhydride to produce a reaction product containing a (meth)acrylic ester and (meth)acrylic acid, wherein a molar ratio of the isosorbide to the (meth)acrylic anhydride is from about 1:1.5 to about 1:2.5;
   ii) reacting said reaction product from step i) with at least one organic compound containing at least one epoxy group to form a reaction product; and
   iii) optionally blending the reaction product from step ii) with up to about 75 wt % of a reactive diluent, based on a total weight of the reaction product from step ii), to produce the curable resin.

2. The method of claim 1, wherein the organic compound containing at least one epoxy group comprises a glycidyl ether.

3. The method of claim 1, wherein the organic compound containing at least one epoxy group comprises at least one compound selected from the group consisting of epoxidized oils, epoxidized cardanol, and epoxidized ricinoleic acid compounds.

4. The method of claim 1, wherein the step ii) is carried out at a temperature of 25° C. to about 100° C.

5. The method of claim 1, wherein the reactive diluent is blended with the reaction product of step ii) and the reactive diluent is selected from the group consisting of: styrene, 2-hydroxymethacrylate, methyl methacrylate, methyl acrylate, furfuryl methacrylate, methacrylated lauric acid, and methacrylated fatty acids.

6. A method of making a cured resin, comprising carrying out the method of claim 1, and further comprising a step of curing the curable resin by free-radical curing to provide the cured resin.

7. The method of claim 6, further comprising a step of curing the curable resin by one of sequential epoxy polymerization, epoxy homopolymerization, epoxy-amine polymerization, and epoxy-anhydride polymerization to provide an interpenetrating polymer network.

8. The method of claim 1, wherein prior to step i) the and the methacrylic anhydride are melted and step i) is carried out in the presence of a basic catalyst.

9. The method of claim 1, wherein the reaction of step i) is carried out until said (meth)acrylic anhydride is consumed.

10. The method of claim 2, A method for producing a curable resin in a one-pot, two step reaction, said method comprising:
   i) reacting an organic compound having at least one hydroxy group with a (meth)acrylic anhydride to produce a reaction product containing a (meth)acrylic ester and (meth)acrylic acid;
   ii) reacting said reaction product from step i) with at least one organic compound containing at least one epoxy group is a glycidyl ether is-selected from the group consisting of diglycidyl ether of bisphenol A, oligomers of diglycidyl ether of bisphenol A, diglycidyl ether of bisphenol F, diglycidyl ether of bisguiaicol F, glycidyl acrylate, glycidyl methacrylate, phenyl glycidyl ether, acrylated glycidyl ethers of bisphenol, methacrylated glycidyl ethers of bisphenol, hydrogenated and brominated versions of the above, and mixtures of any of these chemicals, to form a reaction product; and
   iii) optionally blending the reaction product from step ii) with up to about 75 wt % of a reactive diluent, based on a total weight of the reaction product from step ii), to produce the curable resin.

11. The method of claim 10, wherein the glycidyl ether comprises diglycidyl ether of bisphenol A or oligomers of diglycidyl ether of bisphenol A.

12. The method of claim 10, wherein the glycidyl ether comprises a mixture of diglycidyl ether of bisphenol A and phenyl glycidyl ether in a molar ratio of 0.1 to 99.

13. The method of claim 10, wherein the step ii) has a molar ratio of (meth)acrylic acid to said glycidyl ether of from about 0.1 to about 1.2.

14. The method of claim 10, wherein the step ii) has a molar ratio of (meth)acrylic acid to said glycidyl ether of from about 0.9 to about 1.1.

15. The method of claim 10, wherein the step ii) is carried out at a temperature of 25° C. to about 100° C.

16. The method of claim 10, wherein the reactive diluent is blended with the reaction product of step ii) and the reactive diluent is selected from the group consisting of: styrene, 2-hydroxymethacrylate, methyl methacrylate, methyl acrylate, furfuryl methacrylate, methacrylated lauric acid, and methacrylated fatty acids.

17. The method of claim 10, wherein the organic compound having at least one hydroxy group is selected from a sugar and an alcohol.

18. A method of making a cured resin, comprising carrying out the method of claim 10, and further comprising a step of curing the curable resin by free-radical curing to provide the cured resin.

19. The method of claim 18, further comprising a step of curing the curable resin by one of sequential epoxy polymerization, epoxy homopolymerization, epoxy-amine polymerization, and epoxy-anhydride polymerization to provide an interpenetrating polymer network.

20. The method of claim 1, A method for producing a curable resin in a one-pot, two step reaction, said method comprising:
   i) reacting an organic compound having at least one hydroxy group with a (meth)acrylic anhydride to produce a reaction product containing a (meth)acrylic ester and (meth)acrylic acid, wherein in the step i) a molar ratio of the at least one hydroxy group of the organic compound to the (meth)acrylic anhydride is from about 0.75 to about 1.25 and step i) is carried out in the presence of a basic catalyst;
   ii) reacting said reaction product from step i) with at least one organic compound containing at least one epoxy group to form a reaction product; and
   iii) optionally blending the reaction product from step ii) with up to about 75 wt % of a reactive diluent, based on a total weight of the reaction product from step ii), to produce the curable resin.

21. The method of claim 20, wherein the step ii) is carried out at a temperature of 25° C. to about 100° C.

22. The method of claim 20, wherein the reactive diluent is blended with the reaction product of step ii) and the reactive diluent is selected from the group consisting of: styrene, 2-hydroxymethacrylate, methyl methacrylate, methyl acrylate, furfuryl methacrylate, methacrylated lauric acid, and methacrylated fatty acids.

23. The method of claim 20, wherein the organic compound containing at least one epoxy group comprises a glycidyl ether selected from the group consisting of diglycidyl ether of bisphenol A, oligomers of diglycidyl ether of bisphenol A, diglycidyl ether of bisphenol F, diglycidyl ether of bisguiaicol F, glycidyl acrylate, glycidyl methacrylate, phenyl glycidyl ether, acrylated glycidyl ethers of bisphenol, methacrylated glycidyl ethers of bisphenol, hydrogenated and brominated versions of the above, and mixtures of any of these chemicals.

24. The method of claim 20, wherein the organic compound having at least one hydroxy group is selected from a sugar and an alcohol.

25. The method of claim 20, wherein the organic compound containing at least one epoxy group comprises at least one compound selected from the group consisting of epoxidized oils, epoxidized cardanol, and epoxidized ricinoleic acid compounds.

26. A method of making a cured resin, comprising carrying out the method of claim 20, and further comprising a step of curing the curable resin by free-radical curing to provide the cured resin.

27. The method of claim 26, further comprising a step of curing the curable resin by one of sequential epoxy polymerization, epoxy homopolymerization, epoxy-amine polymerization, and epoxy-anhydride polymerization to provide an interpenetrating polymer network.

* * * * *